United States Patent
Ikada et al.

(10) Patent No.: US 6,831,058 B1
(45) Date of Patent: Dec. 14, 2004

(54) CROSSLINKED GELATIN GEL PREPARATION CONTAINING BASIC FIBROBLAST GROWTH FACTOR

(75) Inventors: Yoshiro Ikada, Kyoto (JP); Yasuhiko Tabata, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 08/567,355

(22) Filed: Nov. 30, 1995

Related U.S. Application Data

(63) Continuation-in-part of application No. PCT/JP94/00876, filed on May 31, 1994.

(30) Foreign Application Priority Data

May 31, 1993 (JP) ............................................. 5-152749
May 31, 1994 (JP) ................................... PCT/JP94/8760

(51) Int. Cl.$^7$ ........................ A61K 38/17; A61K 38/18; C07K 14/50
(52) U.S. Cl. ............................. 514/2; 514/12; 514/944; 514/965; 530/354; 530/399
(58) Field of Search ............................. 514/2, 12, 944, 514/965; 530/399, 354

(56) References Cited

U.S. PATENT DOCUMENTS

| | | | |
|---|---|---|---|
| 3,923,969 A | * 12/1975 | Baukal et al. | 424/19 |
| 4,703,108 A | * 10/1987 | Silver et al. | 530/356 |
| 4,785,079 A | * 11/1988 | Gospodarowicz et al. | 530/399 |
| 4,950,483 A | * 8/1990 | Ksander et al. | 424/422 |
| 5,162,430 A | * 11/1992 | Rhee et al. | 525/54.1 |
| 5,164,410 A | * 11/1992 | Kishimoto et al. | 514/475 |
| 5,270,300 A | * 12/1993 | Hunziker | 514/12 |
| 5,298,243 A | * 3/1994 | Ikada et al. | 424/85.1 |
| 5,614,496 A | * 3/1997 | Dunstan et al. | 514/12 |
| 5,656,598 A | * 8/1997 | Dunstan et al. | 514/12 |

FOREIGN PATENT DOCUMENTS

| | | |
|---|---|---|
| JP | 62228028 | 10/1987 |
| JP | 62289530 | 12/1987 |
| JP | 2049734 | 2/1990 |
| JP | 41282394 | 4/1992 |
| JP | 4279530 | 10/1992 |
| JP | 4330017 | 11/1992 |
| JP | 5124975 | 5/1993 |
| JP | 5132426 | 5/1993 |

OTHER PUBLICATIONS

Dijke et al. Biotech. 7:793–798, 1989.*
Simmons, D.J. Clin. Orthop. Res. 200: 100–113, 1985.*
Ganong, W.F. Review of Medical Physiology, 1989.*
Gospodarowicz et al. Endocr. Rev 8(2): 95–114, 1987.*
Wang et al, "Characterization, Stability, and Formulations of Basic Fibroblast Growth Factor", Plenum Press, New York 1996; pp. 141–180.
Gospodarowicz et al, "Heparin protects basic and acidic FGF from inactivation", J. Cell Physiol Sep. 1986; 128(3):475–84.
Westall et al, "Brain–derived fibroblast growth factor: a study of its inactivation", Life Sci Dec. 12, 1983; 33(24):2425–9.
Gospodarowicz et al. "Structural Characterization and Biological Functions of Fibroblast Growth Factor,", Endocrine Reviews, vol. 8, No. 2, May 1987, pp. 95, 102, 111.

* cited by examiner

Primary Examiner—Christine J. Saoud
(74) Attorney, Agent, or Firm—Nixon & Vanderhye P.C.

(57) ABSTRACT

The present invention relates to a crosslinked gelatin gel preparation containing a basic fibroblast growth factor hereinafter referred to as bFGF wherein a crosslinked gelatin gel is used as a sustained release carrier, and which have different water content, i.e. in vivo degradation and absorption by varying the condition for preparing the crosslinked gelatin gel. By the crosslinked gelatin gel preparation of the present invention, the sustained release rate of bFGF can be varied as required and the durability of in vivo activity of bFGF can be controlled.

12 Claims, 6 Drawing Sheets

○ bFGF - containing crosslinked gelatin gel preparation having a water content of 77.5%
● bFGF - containing crosslinked gelatin gel preparation having a water content of 95.9%

CROSSLINKED GELATIN GEL PREPARATION CONTAINING BASIC FIBROBLAST GROWTH FACTOR

This is a continuation-in-part of PCT/JP94/00876 filed May 31, 1994 having a U.S. designation.

FIELD OF INDUSTRIAL UTILIZATION

The present invention relates to a crosslinked gelatin gel preparation containing a basic fibroblast growth factor (to be abbreviated as "bFGF" hereinafter).

PRIOR ART

In 1976, bFGF was found in bovine pituitary gland by Gospodarowicz as a protein which highly stimulates the proliferation of fibroblast (Nature, Vol. 24, page 124, 1974). Then, bFGF-coding genes have been cloned so that bFGF can be produced in large quantities by genetic recombination technologies, and bFGF has been therefore energetically studied. As a result, it has been revealed that bFGF simulates the proliferation of a variety of cells such as capillary endotherial cells, blood vessel smooth muscle cells, cornea endothelial cells, osteoblast and chondrocyte as well as the proliferation of fibroblast.

Like other polypeptides and proteins, however, bFGF has a short in vivo half-life, and fails to provide an effect as expected when administered as an aqueous solution. It is therefore desirable to formulate bFGF as a sustained release preparation which can stabilize bFGF and can gradually release bFGF for a definite period of time. The present inventors have been therefore engaged in the development of sustained release carriers for formulating bFGF as a sustained release preparation.

In recent years, sustained release preparations of physiologically active peptides and proteins have been extensively studied, and as sustained release carriers therefor, there are synthetic polymers that can undergo degradation by a living body, such as polyglycolic acid.lactic acid and polyanhydride, and natural polymers that can undergo in vivo degradation and absorption, such as polysaccharides and proteins.

PROBLEMS TO BE SOLVED BY THE INVENTION

The natural polymers that can undergo in vivo degradation and absorption have excellent suitability to a living body and cause almost no stimulation to a living body so that they are preferred as sustained release carriers. Since, however, most of these natural polymers are water-soluble, they are not suitable as a sustained release insolubilizing carrier for bFGF which is a water-soluble physiologically active peptide.

The present inventors have therefore made studies for water-insolubilizing natural polymers that can undergo in vivo degradation and absorption, by some method in order to obtain some which can be used as a sustained release insoluble carrier for bFGF.

As a result, it has been found that a crosslinked gelatin gel insolubilized in water by crosslinking a gelatin which is a natural polymer that can undergo in vivo degradation and absorption, is suitable as a sustained release carrier for bFGF, and the present invention has been accordingly completed.

DISCLOSURE OF THE INVENTION

That is, the gist of the present invention consists in a crosslinked gelatin gel preparation containing a basic fibroblast growth factor.

The present invention characteristically provides a sustained release preparation of bFGF, which can achieve a desired sustained release rate as required, on the basis of a crosslinked gelatin gel which has excellent suitability to a living body, causes almost no stimulation on a living body and has excellent properties as a sustained release carrier. The sustained release rate can be varied depending upon the crosslinking degree of a gelatin, the water content of the crosslinked gelatin and the properties of a used gelatin (isoelectric point, etc.).

PREFERRED EMBODIMENTS OF THE INVENTION

Figure 1:
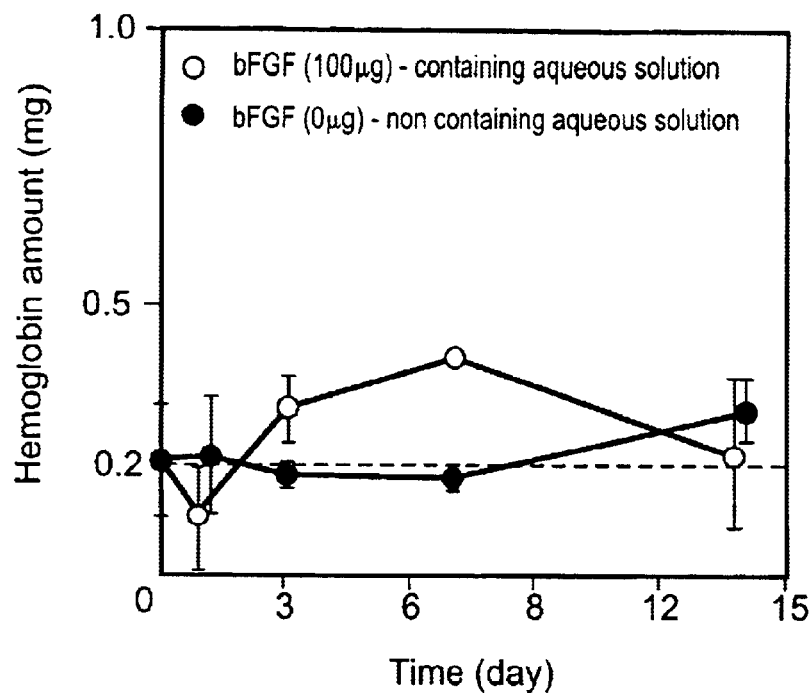
FIG. 1 shows a time course of a hemoglobin amount around the tissue in the mouse subcutaneous administration of a bFGF aqueous solution (bFGF 100 µg).

The present invention will be explained in detail hereinafter.

The crosslinked gelatin gel preparation of the present invention is obtained by incorporating bFGF as an active ingredient into a sustained release crosslinked gelatin gel. The gelatin as a raw material for the crosslinked gelatin gel used in the present invention is not specially limited, and can be selected from generally available ones. Examples of the gelatin include alkali-treated gelatin having an isoelectric point of 4.9 (supplied by Nitta Gelatin Inc.) and acid-treated gelatin having an isoelectric point of 9.0 (supplied by Nitta Gelatin Inc.). As a gelatin, not only one kind of gelatin may be used, but a mixture of gelatins different in physical properties such as solubility, molecular weight, isoelectric point and material may be used.

The crosslinking agent for crosslinking the gelatin, used in the present invention, can be selected from those which are free of toxicity to a living body. For example, it is preferably selected from glutaraldehyde, water-soluble carbodiimides such as 1-ethyl-3-(3-dimethylaminopropyl) carbodiimide hydrochloride and 1-cyclohexyl-3-(2-morpholinoethyl)carbodiimide-metho-p-toluenesulfonate, a bisepoxy compound and formalin. Glutaraldehyde and 1-ethyl-3-(3-dimethylaminopropyl)carbodiimide hydrochloride are particularly preferred.

Further, the gelatin can be crosslinked by heat treatment or irradiation which ultraviolet light.

Although not specially limited in form, the crosslinked gelatin gel as a sustained release carrier used in the present invention has the form, for example, of a cylinder, a prism, a sheet, a disk, spheres or particles. The crosslinked gelatin gel in the form of a cylinder, a prism, a sheet or a disk is generally used for implantation in many cases, and the crosslinked gelatin gel in the form of spheres or particles may be used for the administration by injection as well.

The crosslinked gelatin gel in the form of a cylinder, a prism, a sheet or a disk can be prepared by adding an aqueous solution of the crosslinking agent to a gelatin aqueous solution, or adding the gelatin to an aqueous solution of the crosslinking agent, casting the resultant mixture into a mold having a desired form, and allowing the mixture to react in a crosslinking reaction. Otherwise, and an aqueous solution of the crosslinking agent may be added to gelatin gel obtained by shaping a gelatin as it is or after it is dried. The crosslinking reaction is terminated by bringing the reaction product into contact with a low-molecular-weight substance having an amino group as ethanolamine or glycine, or by adding an aqueous solution having a pH of 2.5 or less. The so-obtained crosslinked gelatin gel is washed with distilled water, ethanol, 2-propanol (to be referred to as "IPA" hereinafter) or acetone, and used for preparing the preparation.

The above-obtained crosslinked gelatin gel has a water content of 50 to 99 w/w % (to be simply denoted by % hereinafter). This water content of a gel shows a ratio of the weight a water content in the gel based on the total gel weight when the gel is wet.

The crosslinking gelatin gel in the form of spheres or particles can be prepared, for example, by either placing an aqueous solution of the gelatin in an apparatus formed of a three-necked flask, a fixed stirrer motor (e.g., three one motor supplied by Shinto Scientific Co., Ltd., EYELA mini D.C. stirrer, or the like) and a stirring propeller of Teflon attached thereto, adding an oil such as olive oil and stirring the mixture at a rate of about 200 to 600 rpm to prepare a W/O emulsion, adding an aqueous solution of the crosslinking agent, or pre-homogenizing a gelatin aqueous solution in an olive oil (e.g., with a vortex mixer Advantec TME-21, a homogenizer polytron PT10-35, or the like), dropwise adding the resultant product in an olive oil to prepare, a finely milled W/O emulsion and adding an aqueous solution of the crosslinking agent, to cause a crosslinking reaction, centrifugally recovering a crosslinked gelatin gel, washing it with acetone or ethyl acetate or the like, and further, immersing the washed crosslinked gelatin gel in IPA ethanol, or the like to terminate the crosslinking reaction. The so-obtained crosslinked gelatin gel is consecutively washed with IPA, distilled water containing Tween 80 and distilled water, and used for preparing the preparation.

When the crosslinked gelatin gel particles from aggregates, for example, they may be ultasonically irradiated (preferably approximately for up to 1 minute with cooling).

In addition, when the pre-emulsification is carried out, there is obtained a crosslinked gelatin gel in the form of fine particles having a particle size of 20 $\mu$m or less.

The obtained crosslinked gelatin gel particles have an average particle diameter of 1 to 1,000 $\mu$m, and are sieved out to necessary sizes as required depending upon purposes. For example, for the topical administration for the therapy of the fracture of a human bone and osteoporosis, it is preferred to use crosslinked gelatin gel particles having a size of 10 to 150 $\mu$m. Further, the obtained crosslinked gelatin gel has a water content of approximately 50 to 93%, and can be prepared as products having water contents as required.

The crosslinked gelatin gel in the form of spheres or particles is also produced by other method as below. An olive oil is placed in an apparatus similar to that in the above method and stirred at a rate of approximately 200 to 600 rpm, and a gelatin aqueous solution is dropwise added thereto to prepare a W/O emulsion. This W/O emulsion is cooled, then acetone, ethyl acetate or the like is added, and the mixture is stirred and centrifugally separated to recover gelatin particles. The recovered gelatin particles are further washed with acetone or ethyl acetate and then with IPA, ethanol or the like, and then dried. The dry gelatin particles are suspended in a crosslinking agent aqueous solution containing 0.1% Tween 80, and the mixture is moderately stirred to cause a crosslinking reaction. The crosslinking reaction is terminated by washing the reaction mixture with a 100 mM glycine aqueous solution containing 0.1% Tween 80 or with 0.004N HCl containing 0.1% Tween 80 depending upon the crosslinking agent used, thereby to obtain crosslinked gelatin gel particles.

The average particle diameter and the water content of the crosslinked gelatin gel particles obtained by this "other" method are similar to those of the crosslinked gelatin gel particles obtained by the above method.

The conditions of the crosslinking reaction should be properly selected as required, while, preferably, the reaction temperature is 0 to 40° C., and the reaction time is 1 to 48 hours.

The above-obtained crosslinked gelatin gel may be further dried under reduced pressure or lyophirized.

The freeze-drying is carried out, for example, by placing the crosslinked gelatin gel in distilled water, freezing it in liquid nitrogen for at least 30 minutes or at −80° C. for at least 1 hour, and then drying it with a freeze-dryer for 1 to 3 days.

The concentrations of the gelatin and the crosslinking agent for the preparation of the crosslinked gelatin gel should be properly selected depending upon a desired water content, while, preferably, the gelatin concentration is 1 to 100 w/v % (to be simply denoted by % hereinafter), and the crosslinking agent concentration is 0.01 to 100 w/v % (to by simply denoted by % hereinafter) equivalent to 1 to 5,400 mM).

The crosslinked gelatin gel can be arranged to have a desired water content by varying the concentrations of the gelatin as a raw material and the crosslinking agent. For increasing the water content, both the gelatin concentration and the crosslinking agent concentration are decreased. For decreasing the water content, conversely, both the gelatin concentration and the crosslinking agent concentration are increased.

For incorporating bFGF into the above-prepared crosslinked gelatin gel, the crosslinked gelatin gel is impregnated with bFGF by dropwise adding a bFGF aqueous solution to the crosslinked gelatin gel, or by suspending the crosslinked gelatin gel in a bFGF aqueous solution to re-shell the crosslinked gelatin gel.

The amount of bFGF which can be incorporated into the crosslinked gelatin gel differs depending upon the water content of the crosslinked gelatin gel, and the like, while bFGF can be incorporated in an amount of 0.1 to 500 μg per mg of the crosslinked gelatin gel.

The sustained release period and the release amount of bFGF differ depending upon various conditions such as the amount of bFGF contained in the preparation, the water content of the crosslinked gelatin gel, physical properties of the gelatin used such as isoelectric point, an administration site, etc.

The bFGF-containing crosslinked gelatin gel obtained in the above manner (to be referred to as "crosslinked gelatin gel preparation" hereinafter) may be lyophilized. When lyophirized, for example, it is frozen in liquid nitrogen for at least 30 minutes or at −80° C. for at least 1 hour, and then dried with a freeze-dryer for 1 to 3 days.

The bFGF used as an active ingredient in the crosslinked gelatin gel preparation of the present invention includes those extracted from organs such as pituitary gland, brain, retina, corpus lutenum, adrenal, kidney, placenta, prostate and thymus, those produced by genetic engineering methods such as recombination DNA technique, and those which are modified products of these and work as fibroblast growth factor. The modified product of bFGF includes those obtained by adding amino acid(s) to the amino acid sequence of bFGF obtained by the above extraction or genetic engineering method, bFGF in which amino acid(s) is partly replaced with other amino acid(s), and bFGF in which amino acid(s) is lacking. In the present invention, these bFGFs or modified products may be used alone or in combination.

Examples of the above bFGF preferably include those disclosed in WO87/01728 (Japanese PCT Publication No. 63-500843), WO89/04832 (Japanese PCT Publication No. 2-504468), WO86/07595 (Japanese PCT Publication No. 63-500036), WO87/03885 (Japanese PCT Publication No. 63-501953), European Laid-open Patent Publication No. 237966 (JP-A-63-226287), European Laid-open Patent Publication No. 281822 (JP-A-193), European Laid-open Patent Publication No. 326907 (JP-A-2-209894), European Laid-open Patent Publication No. 394851 (JP-A-3-61494) and European Laid-open Patent Publication No. 493737 (JP-A-5-124975).

Of the above bFGFs, a polypeptide having a sequence of 154 amino acids in the following SEQ ID No. 1 and a polypeptide having a sequence of 153 amino acids in the following SEQ ID No. 2, produced by a genetic engineering method and disclosed in WO87/01728, are particularly preferred in view of stability and availability of a necessary amount on a constant basis.

bFGF having the amino acid sequence shown in the SEQ ID No. 1 is obtained by preparing a cDNA clone of human bFGF from a $\lambda_{gt}10$cDNA library prepared from mRNA of human kidney using bovine 1.4 kb basic sub-fragment, and constituting an expression vector to express the above clone, as is described in Japanese PCT Publication No. 63-500843.

```
SEQ ID No.:1
Sequence characteristics:
Sequence length: 154 amino acids
Sequence type: amino acid
Original source
Organism: Homo sapiens
Sequence Ala Ala Gly Ser Ile Thr Thr Leu Pro Ala Leu Pro Glu Asp Gly Gly
1             5                  10                 15

Ser Gly Ala Phe Pro Pro Gly His Phe Lys Asp Pro Lys Arg Leu Tyr
             20              25              30

Cys Lys Asn Gly Gly Phe Phe Leu Arg Ile His Pro Asp Gly Arg Val
         35              40              45

Asp Gly Val Arg Glu Lys Ser Asp Pro His Ile Lys Leu Gln Leu Gln
     50              55              60

Ala Glu Glu Arg Gly Val Val Ser Ile Lys Gly Val Cys Ala Asn Arg
65              70              75              80

Tyr Leu Ala Met Lys Glu Asp Gly Arg Leu Leu Ala Ser Lys Cys Val
             85              90              95

Thr Asp Glu Cys Phe Phe Glu Arg Leu Glu Ser Asn Asn Tyr Asn
             100             105             110

Thr Tyr Arg Ser Arg Lys Tyr Thr Ser Trp Tyr Val Ala Leu Lys Arg
         115             120             125

Thr Gly Gln Tyr Lys Leu Gly Ser Lys Thr Gly Pro Gly Gln Lys Ala
     130             135             140

Ile Leu Phe Leu Pro Met Ser Ala Lys Ser
145                 150

SEQ ID No.:2
Sequence characteristics:
Sequence length: 153 amino acids
Sequence type: amino acid
Original source
```

-continued

Organism: Homo sapiens
Sequence

```
Ala Gly Ser Ile Thr Thr Leu Pro Ala Leu Pro Glu Asp Gly Gly Ser
 1               5                  10                  15

Gly Ala Phe Pro Pro Gly His Phe Lys Asp Pro Lys Arg Leu Tyr Cys
            20                  25                  30

Lys Asn Gly Gly Phe Phe Leu Arg Ile His Pro Asp Gly Arg Val Asp
        35                  40                  45

Gly Val Arg Glu Lys Ser Asp Pro His Ile Lys Leu Gln Leu Gln Ala
     50                  55                  60

Glu Glu Arg Gly Val Val Ser Ile Lys Gly Val Cys Ala Asn Arg Tyr
 65                  70                  75                  80

Leu Ala Met Lys Glu Asp Gly Arg Leu Leu Ala Ser Lys Cys Val Thr
             85                  90                  95

Asp Glu Cys Phe Phe Phe Glu Arg Leu Glu Ser Asn Asn Tyr Asn Thr
                100                 105                 110

Tyr Arg Ser Arg Lys Tyr Thr Ser Trp Tyr Val Ala Leu Lys Arg Thr
            115                 120                 125

Gly Gln Tyr Lys Leu Gly Ser Lys Thr Gly Pro Gly Gln Lys Ala Ile
        130                 135                 140

Leu Phe Leu Pro Met Ser Ala Lys Ser
145                 150
```

EXAMPLES

The present invention will be explained in detail hereinafter which reference to Examples and Test Examples, while the present invention shall not be limited to these Examples and Test Examples.

(Example 1)

An aqueous solution of 1-ethyl-3-(2-dimethylaminopropyl)carbodiimide hydrochloride (supplied by Dojindo Laboratories, to be abbreviated as WSC hereinafter) (2.0%, equivalent to 107 mM) was added to 450 μl of an aqueous solution of alkali-treated gelatin having an isoelectric point of 4.9 (supplied by Nitta Gelatin Inc.) (5.6%), and the mixture was cast into a cylindrical mold having a diameter of 8 mm and maintained at 4° C. for 24 hours to carry out a crosslinking reaction. After the reaction, the reaction mixture was treated in 0.004N HCl at 37° C. for 1 hour, and the crosslinking reaction was terminated. The so-obtained crosslinked gelatin gel was washed with distilled water at 37° C. for 12 hours. The water content of the gel was measured on the basis of a difference between the weight of the crosslinked gelatin gel after the swelling treatment in water at 37° C. for 24 hours, and the weight of the gelatin gel before the swelling treatment, to show 95.9%. The resultant cylindrical gel was cut into disks having a thickness of 2 mm, and dried. To the dry gel was dropwise added 30 μl of a 50 mM phosphate buffer solution (pH 6.0) containing 100 μg of bFGF, and the resultant disks were allowed to stand at 4° C. for a whole day and night, to give bFGF-containing crosslinked gelatin gel preparations in which the crosslinked gelatin gel was impregnated with 100 μg of bFGF.

(Example 2)

Crosslinked gelatin gel preparations containing bFGF were prepared in the same manner as in Example 1 except that acid-treated gelatin having an isoelectric point of 9.0 (supplied by Nitta Gelatin Inc.) (5.6%). The crosslinked gelatin gel had a water content of 95.2%.

(Example 3)

Crosslinked gelatin gel preparations containing bFGF were prepared in the same manner as in Example 1 except that the WSC concentration was changed to 8.0% (equivalent to 428 mM). The crosslinked gelatin gel had a water content of 95.2%.

(Example 4)

Crosslinked gelatin gel preparations containing bFGF were prepared in the same manner as in Example 1 except that the gelatin concentration was changed to 11.1% and that the WSC concentration was changed to 16.4% (equivalent to 856 mM). The crosslinked gelatin gel had a water content of 92.1%.

(Example 5)

A WSC aqueous solution having a concentration shown in Table 1 to be described later was added to an aqueous solution of alkali-treated gelatin having an isoelectric point of 4.9 (supplied by Nitta Gelatin Inc.) with a concentration shown in the Table 1, and then the mixture was cast into a cylindrical mold having a diameter of 8 mm and subjected to a crosslinking reaction at 4° C. for 24 hours. After the reaction, the reaction mixture was treated in 0.004N HCl at 37° C. and the crosslinking reaction was terminated. The so-obtained crosslinked gelatin gel was washed with distilled water at 37° C. for 12 hours. The water content of the gel was measured on the basis of a difference between the weight of the crosslinked gelatin gel after the swelling treatment in water at 37° C. for 24 hours, and the weight of the gelatin gel before the swelling treatment. Table 1 shows the water content of each of the so-obtained crosslinked gelatin gels. Each resultant cylindrical gel was cut into disks having a thickness of 2 mm, and dried. To the dry gel was dropwise added 30 µl of a 50 mM phosphate buffer solution (pH 6.0) containing 100 µg of bFGF, and the resultant disks were allowed to stand at 4° C. for a whole day and night, to impregnate each gelatin gel with 100 µg of bFGF, whereby bFGF-containing crosslinked gelatin gel preparations were obtained.

(Example 6)

A crosslinked gelatin gel having a water content of 63.1% was obtained by immersing the cylindrical crosslinked gelatin gel having a water content of 80.0%, obtained in the above Example 5, in a WSC aqueous solution (9.6%, equivalent to 500 mM) for 24 hours. The so-obtained crosslinked gelatin gel having a water content of 63.1% was out into disks having a thickness of 2 mm, and dried. To the dry gel was dropwise added 30 µl of a 50 mM phosphate buffer solution (pH 6.0) containing 100 µg of bFGF, and the resultant disks were allowed to stand at 4° C. for a whole day and night, to impregnate the gelatin gel with 100 µg of bFGF, whereby bFGF-containing crosslinked gelatin gel preparations were obtained.

(Example 7)

Crosslinked gelatin gels were contained by carrying out crosslinking reactions in the same manner as in Example 5 except that WSC aqueous solutions having concentrations shown in Table 1 to be described later were added to gelatin aqueous solutions having concentrations shown in Table 1. Table 1 shows the water contents of the so-obtained crosslinked gelatin gels. Each cylindrical gelatin gel as obtained was out into disks having a thickness of 2 mm, and dried. To each dry gel was dropwise added 30 µl of a 50 mM phosphate buffer solution (pH 6.0) containing 100 µg of bFGF, and the resultant disks were allowed to stand at 4° C. for a whole day and night, to impregnate each gelatin gel with 100 µg of bFGF, whereby bFGF-containing crosslinked gelatin gel preparations were obtained.

(Example 8)

A crosslinked gelatin gel having a water content of 68.9% was obtained by immersing the cylindrical crosslinked gelatin gel having a water content of 78.5%, obtained in the above Example 7, in a WSC aqueous solution (9.6%, equivalent to 500 mM) for 24 hours. The so-obtained crosslinked gelatin gel having a water content of 68.9% was cut into disks having a thickness of 2 mm, and dried. To the dry gel was dropwise added 30 µl of a 50 mM phosphate buffer solution (pH 6.0) containing 100 µg of bFGF, and the resultant disks were allowed to stand at 4° C. for a whole day and night, to impregnate the gelatin gel with 100 µg of bFGF, whereby bFGF-containing crosslinked gelatin gel preparations were obtained.

(Example 9)

A 0.9-ml aqueous solution of alkali-treated gelatin having an isoelectric point of 4.9 (supplied by Nitta Gelatin Inc.) (5.6%) was added to 250 ml of an olive oil, and the mixture was stirred at room temperature at a rate of 450 rpm to prepare a W/O emulsion. To this emulsion was added 0.1 ml of a WSC aqueous solution (16.4%, equivalent to 856 mM), and the mixture was continuously stirred for a whole day and night to crosslink the gelatin, whereby crosslinked gelatin gel particles were obtained. The so-obtained crosslinked gelatin gel particles had an average particle diameter of 30 µm and had a water content of 96.0%. The particles were dried, and then 10 mg of the dry particles were immersed in 30 µl of a 50 mM phosphate buffer solution (pH 6.0) containing 100 µg of bFGF, and allowed to stand at 4° C. for a whole day and night, to impregnate the gelatin gel particles with the bFGF, whereby bFGF-containing crosslinked gelatin gel particle preparations were obtained.

(Example 10)

An olive oil in an amount of 250 ml was placed in a three-necked flask having a volume of 500 ml, and the flask was fixed together with a fixed stirrer motor (three one motor, supplied by Shinto Scientific Co., Ltd.) equipped with a stirring propeller of Teflon. Separately, 5 ml of an olive oil was taken and warmed up to 45° C., and 0.9 ml of an aqueous solution of alkali-treated gelatin having an isoelectric point of 4.9 (supplied in Nitta Gelatin Inc.) (11.1%) was added. The mixture was pre-emulsified with a homopolymer (Polytron PT-35) for 30 seconds. This pre-emulsified emulsion was added to the oliver oil which had been preliminarily stirred, to give a W/O emulsion, A WSC aqueous solution (27.0%, equivalent to 1,424 mM) in an amount of 0.1 ml was added, and the mixture was continuously stirred for about 15 hours to crosslink the gelatin. After the crosslinking reaction, 50 ml of acetone was added, and the mixture was stirred for 1 hour and then centrifugally separated to recover crosslinked gelatin gel particles. The so-recovered gelatin gel particles were washed with acetone (centrifuge 3,000 rpm, operation for 5 minutes five times), and further, immersed in 2-propanol (to be referred to as IPA hereinafter) containing 0.004N HCl at 37° C. for 1 hour to terminate the crosslinking reaction under remaining WSC. After the termination of the reaction, these crosslinked particles were washed with IPA (centrifuge 3,000 rpm, operation for 5 minutes five times). Further, the crosslinked particles were washed with distilled water containing 0.01% of Tween 80 (centrifuge 2,000 rpm, 5 minutes) once, washed with distilled water (centrifuge 2,000 rpm, 5 minutes) twice, and lyophirized to give a dry powder of the crosslinked gelatin gel particles (average particle diameter 4 µm, water content 91.0%).

30 Microliters of a 1/15 M phosphate buffer solution containing 3.3 mg/ml of bFGF (pH 6) was dropwise added to 10 mg of the above-obtained crosslinked gelatin gel particles, and the particles were allowed to stand at 4° C. for a whole day and night to impregnate the particles with the bFGF aqueous solution, whereby bFGF-containing crosslinked gelatin gel particle preparations were obtained. The so-obtained bFGF-containing crosslinked gelatin gel particle preparations were lyophirized to give bFGF-containing dry crosslinked gelatin gel particle preparations.

(Example 11)

10 Microliters of a 20 mM citric acid buffer solution containing 8 mg/ml of bFGF (pH 5) was dropwise added to 2 mg of the dry crosslinked gelatin gel particles obtained in the above Example 10, and the particles were allowed to stand at 4° C. for a whole day and night to impregnate the particles with the bFGF aqueous solution, whereby bFGF-containing crosslinked gelatin gel particle preparations were obtained. The so-obtained bFGF-containing crosslinked gelatin gel particle preparations were lyophirized to give bFGF-containing dry crosslinked gelatin gel particle preparations.

(Example 12)

200 Microliters of an aqueous solution containing 1 mg/ml of bFGF was added to 10 mg of the dry crosslinked gelatin gel particles obtained in the above Example 10, and the mixture was allowed to stand at room temperature for 1 hour to allow the bFGF aqueous solution to be adsorbed into the particles, whereby bFGF-containing gelatin particle preparations were obtained. The so-obtained bFGF-containing crosslinked gelatin gel particle preparations were lyophirized to give bFGF-containing dry crosslinked gelatin gel particle preparations.

(Example 13)

An olive oil in an amount of 375 ml was placed in a three-necked flask having a volume of 1,000 ml, and the flask was fixed together with a fixed stirrer motor (three one motor, supplied by Shinto Scientific Co., Ltd.) equipped with a stirring propeller of Teflon. While the olive oil was stirred at 30° C. at a rate of 420 rpm, 10 ml of an aqueous solution of alkali-treated gelatin (10.0%) having an isoelectric point of 4.9 was dropwise added to prepare a W/O emulsion. After the mixture was stirred for 10 minutes, the flask was cooled to 10–20° C., and the mixture was stirred for 30 minutes. After the mixture was cooled, 100 ml of acetone was added thereto, and the mixture was stirred for 1 hour and then centrifugally separated to recover gelatin particles. The recovered gelatin particles were washed with acetone, and further washed with IPA to give non-crosslinked gelatin particles. The non-crosslinked gelatin particles were dried, and stored at 4° C.

The dry non-crosslinked gelatin particles in an amount of 500 mg were suspended in 100 ml of an aqueous solution of glutaraldehyde (to be referred to as GA hereinafter) (0.05%, equivalent to 5.0 mM) containing 0.1% Tween 80, and the suspension was moderately stirred at 4° C. for 15 hours to cause a crosslinking reaction. After the reaction, the crosslinked particles were centrifugally recovered, and washed with a 100 mM glycine aqueous solution containing 0.1% Tween 80 at 37° C. for 1 hour to terminate the crosslinking reaction. After the reaction was terminated, the crosslinked particles were consecutively washed with a 0.1% Tween 80 aqueous solution, with IPA and with a 0.1% Tween 80 aqueous solution, washed with distilled water twice, and then lyophirized to give dry crosslinked gelatin gel particles (average particle diameter 40 $\mu$m, water content 87.0%).

30 Microliters of a $\frac{1}{15}$ M phosphate buffer solution containing 3.3 mg/ml of bFGF (pH 6) was dropwise added to 10 mg of the above-obtained dry crosslinked gelatin gel particles, and the mixture was allowed to stand 4° C. at for a whole day and night to impregnate the particles with the bFGF aqueous solution, whereby bFGF-containing crosslinked gelatin gel particle preparations were obtained. The so-obtained bFGF-containing crosslinked gelatin gel particles preparations were lyophirized to give bFGF-containing dry crosslinked gelatin gel particle preparations.

(Example 14)

10 Microliters of a 20 mM citric acid buffer solution containing 8 mg/ml of bFGF (pH 5) was dropwise added to 2 mg of the dry crosslinked gelatin gel particles obtained in Example 13, and the mixture was allowed to stand at 4° C. for a whole day and night to impregnate the particles with the bFGF aqueous solution, whereby bFGF-containing crosslinked gelatin gel particle preparations were obtained. The so-obtained bFGF-containing crosslinked gelatin gel particle preparations were lyophirized to give bFGF-containing dry crosslinked gelatin gel particle preparations.

(Example 15)

200 Microliters of an aqueous solution containing 1 mg/ml of bFGF was added to 10 mg of the dry crosslinked gelatin gel particles obtained in Example 13 to form a suspension, and the suspension was allowed to stand at room temperature for 1 hour to allow the bFGF aqueous solution to be adsorbed into the particles, whereby bFGF-containing crosslinked gelatin gel particle preparations were obtained. The so-obtained bFGF-containing crosslinked gelatin gel particle preparations were lyophirized to give bFGF-containing dry crosslinked gelatin gel particle preparations.

(Example 16)

20 Millliliters of an aqueous solution of alkali-treated gelatin having an isoelectric point of 4.9 (supplied by Nitta Gelatin Inc.) (10.0%) was poured into a petri dish having a diameter of 10 cm and dried, and the resultant dry gelatin sheet was immersed in a WSC aqueous solution (0.04%, equivalent to 2.0 mM) and maintained at 4° C. for 24 hours to carry cut a crosslinking reaction. After the reaction finished, the reaction mixture was treated in 0.004N HCl at 37° C. for 1 hour to terminate the crosslinking reaction, and further washed with distilled water at 37° C. for 12 hours to give a crosslinked gelatin gel. This gel was cut into disks having a size a 4×3×2 mm and dried under reduced pressure. The so-obtained gel had a water content of 87.0%.

10 Microliters of an aqueous solution containing 200 $\mu$g/ml of bFGF, or 10 $\mu$l of an aqueous solution containing 1 mg/ml of bFGF, was dropwise added to the above dry crosslinked gelatin gel, and the dry crosslinked gelatin gel was impregnated therewith at 4° C. for 15 hours to give two kinds of bFGF-containing crosslinked gelatin gel preparations.

Table 1 shows the prescriptions of the bFGF-containing crosslinked gelatin gel preparations and bFGF-containing crosslinked gelatin gel particle preparations obtained in the above Examples 1 to 16 and the water contents of the obtained crosslinked gelatin gels.

In Table 1, WSC and GA as crosslinking agents stand for 1-ethyl-3-(3-dimethylaminopropyl)carbodiimide hydrochloride and glutaraldehyde respectively. The concentrations % of gelatins and the crosslinking agents in the Table respectively show "w/v %", and the water content % stands for "w/w %".

TABLE 1

| Example No. | Gelatin | Crosslinking agent | Water content (%) | Final form | bFGF content |
|---|---|---|---|---|---|
| 1 | Alkali-treated gelatin having isoelectric point of 4.9 5.6% | WSC 2.0% (107 mM) | 95.9% | disk-shaped | 100 μg/ preparation |
| 2 | Acid-treated gelatin having isoelectric point of 9.0 5.6% | WSC 2.0% (107 mM) | 95.2% | " | 100 μg/ preparation |
| 3 | Alkali-treated gelatin having isoelectric point of 4.9 5.6% | WSC 8.0% (428 mM) | 95.2% | " | 100 μg/ preparation |
| 4 | Alkali-treated gelatin having isoelectric point of 4.9 11.1% | WSC 16.4% (856 mM) | 92.1% | " | 100 μg/ preparation |
|  | Alkali-treated gelatin having isoelectric point of 4.9 5.6% | WSC 2.0% (107 mM) | 95.9% | " | 100 μg/ preparation |
|  | Alkali-treated gelatin having isoelectric point of 4.9 11.1% | WSC 16.4% (856 mM) | 92.1% | " | 100 μg/ preparation |
| 5 | Alkali-treated gelatin having isoelectric point of 4.9 11.1% | WSC 27.0% (1,424 mM) | 87.6% | " | 100 μg/ preparation |
|  | Alkali-treated gelatin having isoelectric point of 4.9 33.3% | WSC 80.0% (4,278 mM) | 80.0% | " | 100 μg/ preparation |
|  | Alkali-treated gelatin having isoelectric point of 4.9 33.3% | WSC 85.0% (4,568 mM) | 77.5% | " | 100 μg/ preparation |
| 6 | Crosslinked gelatin gel having water content of 80.0% obtained in Example 5 | WSC 9.6% (500 mM) | 63.1% | " | 100 μg/ preparation |
|  | Alkali-treated gelatin having isoelectric point of 4.9% 5.6% | WSC 2.0% (107 mM) | 96.8% | " | 100 μg/ preparation |
| 7 | Alkali-treated gelatin having isoelectric point of 4.9% 11.1% | WSC 16.4% (856 mM) | 91.5% | " | 100 μg/ preparation |
|  | Alkali-treated gelatin having isoelectric point of 4.9% 33.3 | WSC 85.0% (4,568 mM) | 78.5% | " | 100 μg/ preparation |
| 8 | Crosslinked gelatin gel having water content of 78.5% obtained in Example 7 | WSC 9.6% (500 mM) | 68.9% | " | 100 μg/ preparation |
| 9 | Alkali-treated gelatin having isoelectric point of 4.9 5.6% | WSC 16.4% (856 mM) | 96.0% | Particulate (average particle diameter: 30 μm) | 100 μg/dry particles 10 mg |
| 10 | Alkali-treated gelatin having isoelectric point of 4.9 11.1% | WSC 27.0% (1,424 mM) | 91.0% | dry particulate (average particle diameter: 4 μm) | 100 μg/dry particles 10 mg |
| 11 | Alkali-treated gelatin having isoelectric point of 4.9 11.1% | WSC 27.0% (1,424 mM) | 91.0% | dry particulate (average particle diameter: 4 μm) | 80 μg/dry particles 2 mg |
| 12 | Alkali-treated gelatin having isoelectric point of 4.9 11.1% | WSC 27.0% (1,424 mM) | 91.0% | dry particulate (average particle diameter: 4 μm) | 200 μg/dry particles 10 mg |
| 13 | Alkali-treated gelatin having isoelectric point of 4.9 10.0% | GA 0.05% (5.0 mM) | 87.0% | dry particulate (average particle diameter: 40 μm) | 100 μg/dry particles 10 mg |

TABLE 1-continued

| Example No. | Gelatin | Crosslinking agent | Water content (%) | Final form | bFGF content |
|---|---|---|---|---|---|
| 14 | Alkali-treated gelatin having isoelectric point of 4.9 10.0% | GA 0.05% (5.0 mM) | 87.0% | dry particulate (average particle diameter: 40 μm) | 80 μg/dry particles 2 mg |
| 15 | Alkali-treated gelatin having isoelectric point of 4.9 10.0% | GA 0.05% (5.0 mM) | 87.0% | dry particulate (average particle diameter: 40 μm) | 200 μg/dry particles 10 mg |
| 16 | Alkali-treated gelatin having isoelectric point of 4.9 10.0% | WSC 0.04% (2.0 mM) | 87.0% | disk-shaped | (1) 2 μg/preparation (2) 10 μg/preparation |

(Test Example 1)

The bFGF-containing crosslinked gelatin gel preparation obtained in Example 1 was subcutaneously implanted in back portions of mice. Separately, as a control group, a crosslinked gelatin gel which contained no bFGF but was impregnated with 30 μl of a 50 mM phosphate buffer solution containing no bFGF was subcutaneously implanted. Further, as another control group, 100 μl of a phosphate buffer solution containing 100 μg of bFGF was subcutaneously administered. One week after the administration, mouse skins were peeled off to observe sites where the preparation had been implanted and the phosphate buffer solution had been administered. In the group of mice which had been administered with the bFGF-containing phosphate buffer solution, the state of tissue around the administration site was the same as that of an untreated group, and no change was visually found. In the case where bFGF-containing crosslinked gelatin gel preparation had been implanted, the tissue around the preparation-implanted site was visually red, and a vascularization effect, one of the bFGF activities, was clearly found. In the group of mice which had been administered with the crosslinked gelatin gel containing no bFGF, the tissue around the implanted site was like that of the untreated group and showed no vascularization.

The above results show the following. In the group of mice which are administered with a phosphate buffer solution containing bFGF, no pharmacological effect of bFGF is obtained. That is, when a bFGF aqueous solution is administered, the bFGF is rapidly degradated in a living tissue to lose its pharmacological effect. In contrast, when the bFGF-containing crosslinked gelatin gel preparation is used, the bFGF undergoes sustained release from the crosslinked gelatin gel as a carrier without being degradated in a living tissue, and can exhibit and retain its pharmacological effect. Further, it is seen that the crosslinked gelatin gel is excellent in suitability to a living body.

(Test Example 2)

Figure 2:
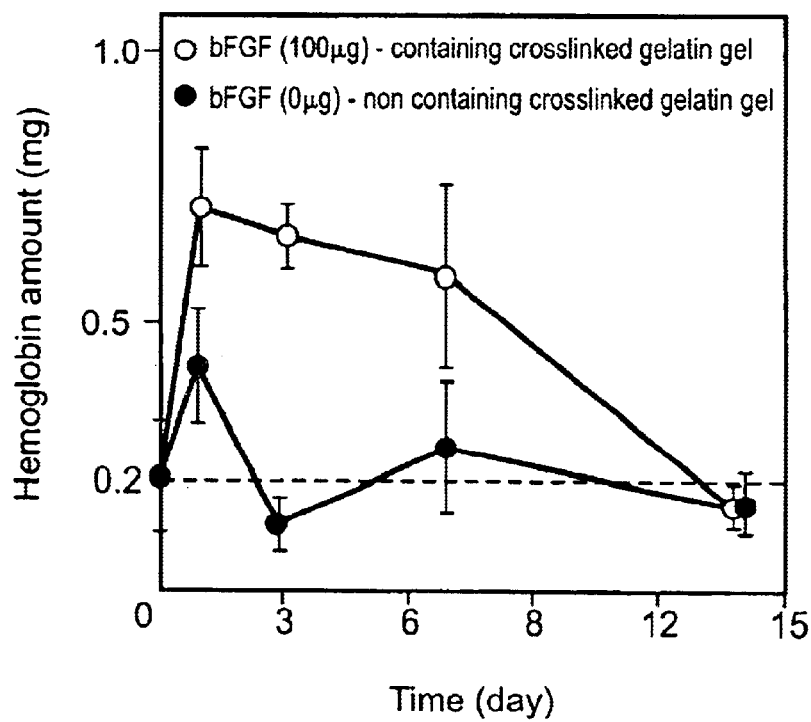
FIG. 2 shows a time course of a hemoglobin amount in peripheral tissue in the mouse subcutaneous implantation of a crosslinked gelatin gel (water content 95.9%) preparation (bFGF 100 µg).

The bFGF-containing crosslinked gelatin gel preparation obtained in Example 1 was subcutaneously implanted in mice, and the degree of vascularization around the implanted site was evaluated 1, 3, 7 and 14 days after the administration on the basis of a change in the amount of hemoglobin as an index. Separately, as control groups, the degree of vascularization was similarly evaluated concerning each of a group of mice in which a crosslinked gelatin gel containing no bFGF was subcutaneously implanted bFGF (−) crosslinked gelatin gel administration group), a group of mice which were subcutaneously administered with a phosphate buffer solution containing 100 mg of bFGF by injection (bFGF (+) aqueous solution administration group) and a group of mice which were administered with a phosphate buffer solution containing no bFGF by injection (bFGF (−) aqueous solution administration group). The neovascularization was evaluated as follows. Tissues below the skin of the preparation-implanted site or the injection-administration site and on the nortal-muscular side were scraped off with a scalpel such that the scraped portion had a square form measuring 2 cm horizontally and vertically with the preparation-implanted site or the injection administration site as a center. These tissues were immersed in a 17 mM Tris-HCl buffer solution (pH 7.6) containing 0.75% ammonium chloride, to extract hemoglobin. The hemoglobin was quantitatively determined by a cyanmethamoglobin method (Hemoglogin-Test Wako, supplied by Wako Pure-chemical Co., Ltd.). The number of mice per group was five. FIGS. 1 and 2 show a time course of the hemoglobin amount in each group. The dotted line in each Figure shows the hemoglobin amount of the untreated group. The administration with 100 μg of bFGF alone in a solution state did not cause any change in the hemoglobin amount around the tissue, and the hemoglobin amount was at the same level as that when the phosphate buffer solution containing no bFGF had been administered. This hemoglobin level was the same as that of the hemoglobin amount of the untreated group. However, when the crosslinked gelatin gel containing the same amount, 100 μg, of bFGF was implanted, the hemoglobin amount significantly increased from the third day from the implantation, onward, as compared with the group of mice to which 100 μg of bFGF in a solution state had been administered. Further, this state continued up to the 7th day, and the hemoglobin amount decreased to the hemoglobin level of the untreated group on the 14th day. On the other hand, in the bFGF (−) crosslinked gelatin gel administration group, the hemoglobin amount was at the same level as that of the untreated group.

(Test Example 3)

Figure 3:
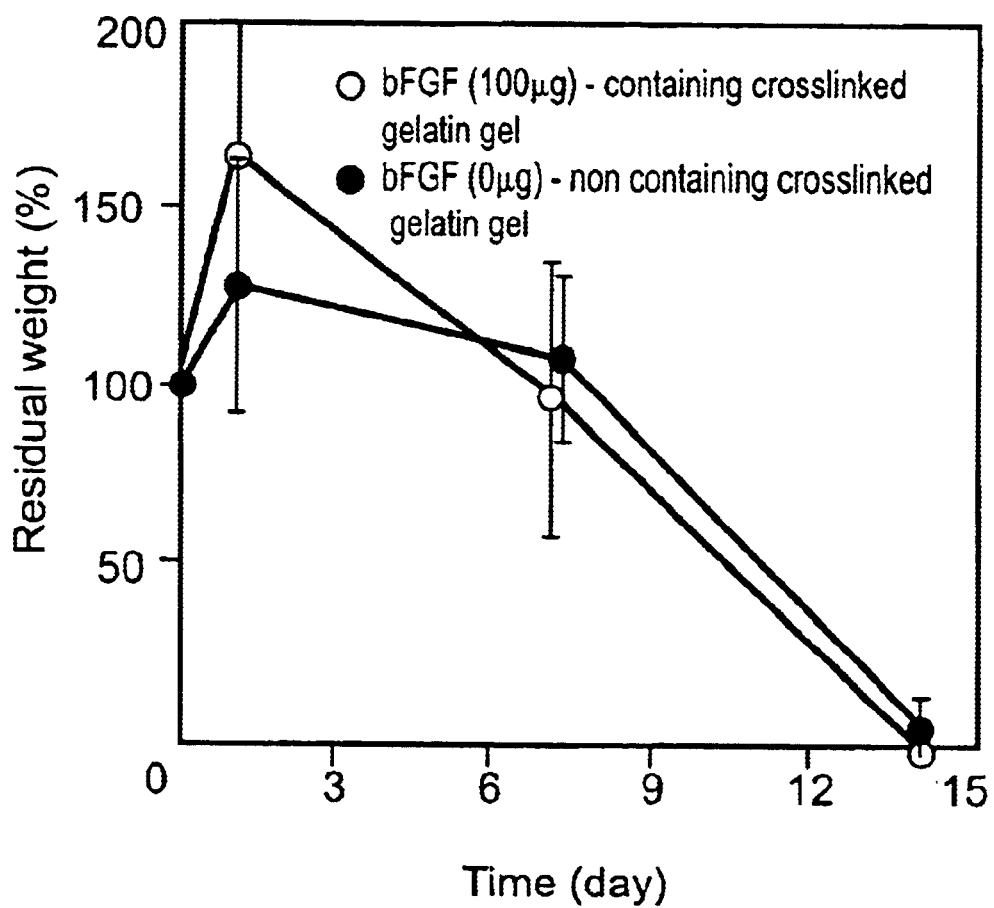
FIG. 3 shows a time course of the residual weight of a crosslinked gelatin gel (water content 95.2%) preparation (bFGF 100 µg) subcutaneously implanted in a mouse.

The bFGF-containing crosslinked gelatin gel preparations (water content 95.2%) obtained in Example 3 were subcutaneously implanted in back portions of mice, and measured for remaining crosslinked gelatin gel weights on the 1st, 7th and 14 days from the administration, to evaluate the in vivo degradation of the gel. The crosslinked gelatin gel was degradated with the passage of time, and on the 14th day from the administration, the gel was completely degradated and absorbed into the tissue. Further, the degradation of the crosslinked gelatin gel containing no bFGF was the same as that of the bFGF-containing crosslinked gelatin gel, and no influence of the incorporation of bFGF on the degradation of the crosslinked gelatin gel was observed. FIG. 3 shows the results. It is presumably because the subcutaneous tissue adhered to the crosslinked gelatin gel when the crosslinked gelatin gel was recovered from the subcutaneous sites of the mice that the remaining amounts were larger than those at the administration time, or over 100%, for several days after the administration.

The bFGF-containing crosslinked gelatin gel preparation (water content 95.9%) which showed a vascularization effect in Example 1 exhibited similar decomposition behavior.

(Test Example 4)

Figure 4:
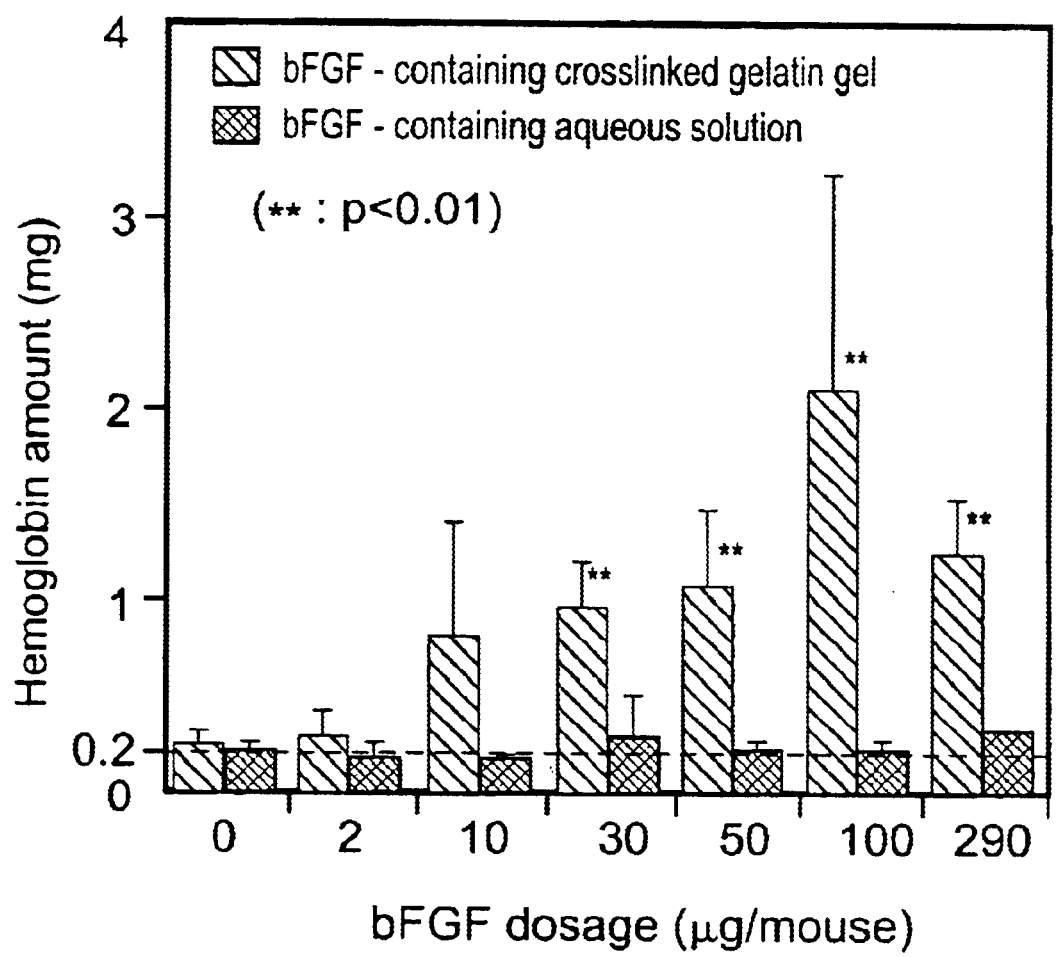
FIG. 4 shows a relationship between the dose of bFGF and the hemoglobin amount in a tissue in the periphery of an administration site.

The crosslinked gelatin gel prepared in Example 4 was dried, and then immersed in a phosphate buffer solution (pH 6.0) containing 0, 2, 10, 30, 50, 100 or 290 μg of bFGF to prepare a crosslinked gelatin gel preparation containing no bFGF and crosslinked gelatin gel preparations having the above concentrations of bFGF. These preparations were implanted in back portions of mice, and 7 days after the administration hemoglobin amounts around the preparation-implanted sites were evaluated. FIG. 4 shows the results. The dotted line in FIG. 4 shows the hemoglobin level of an untreated group. As control groups, a phosphate buffer solution containing 0, 2, 10, 30, 50, 100 or 290 μg of bFGF was subcutaneously administered to mice. When the bFGF solutions were administered, there was not observed any increase in the hemoglobin amount in any dosage, having nothing to do with their dosage. In contrast, according to the preparations of the present invention in which bFGF was contained in the crosslinked gelatin gel, a significant increase in the hemoglobin amount was observed, and the bFGF dosage of 10 μg/mouse or more showed its effect.

(Test Example 5)

Figure 5:
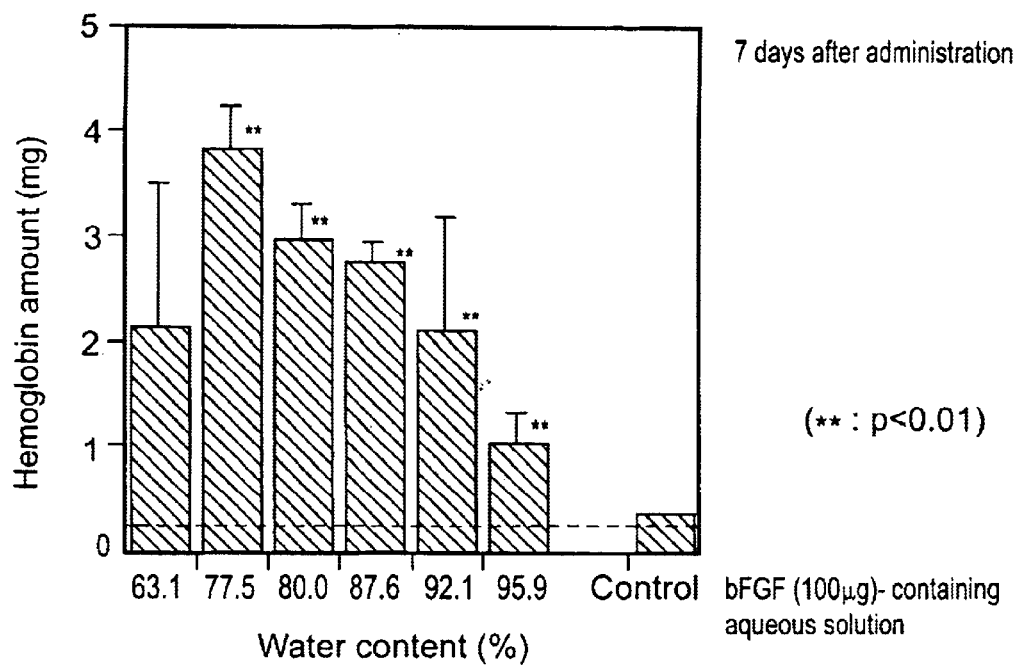
FIG. 5 shows a relationship between the hemoglobin amount in a tissue in the periphery of an implanted site and the water content of a crosslinked gelatin gel on the 7th day after subcutaneous implantation of a crosslinked gelatin gel preparation (bFGF 100 µg) in a mouse.
Figure 6:
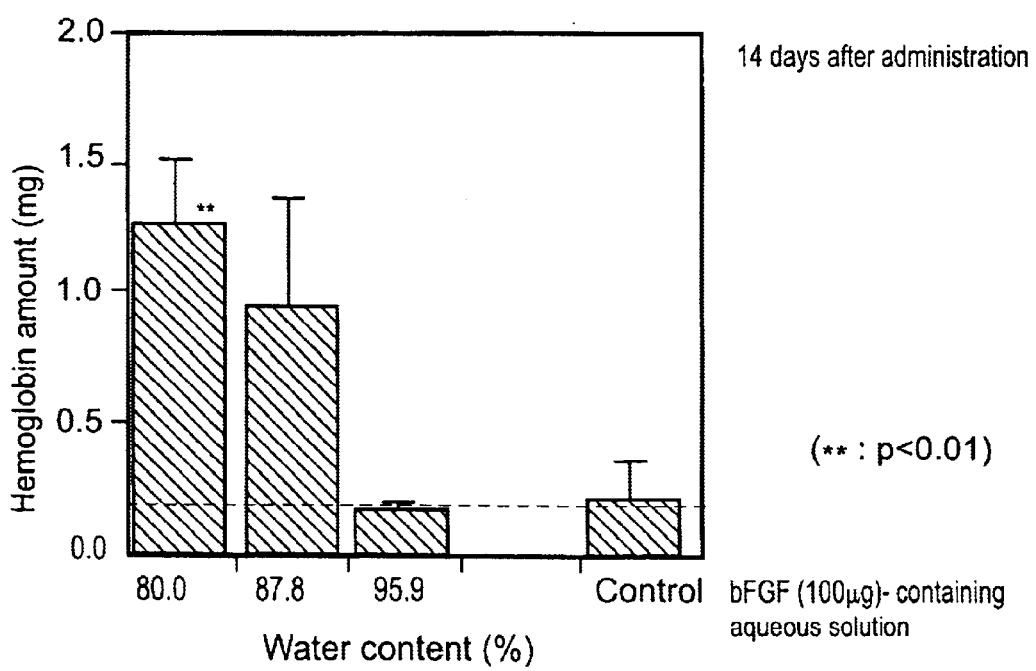
FIG. 6 shows relationship between the hemoglobin amount in a tissue in the periphery of an implanted site and the water content of a crosslinked gelatin gel on the 14th day after subcutaneous implantation of a crosslinked gelatin gel preparation (bFGF 100 µg) in a mouse.
Figure 7:
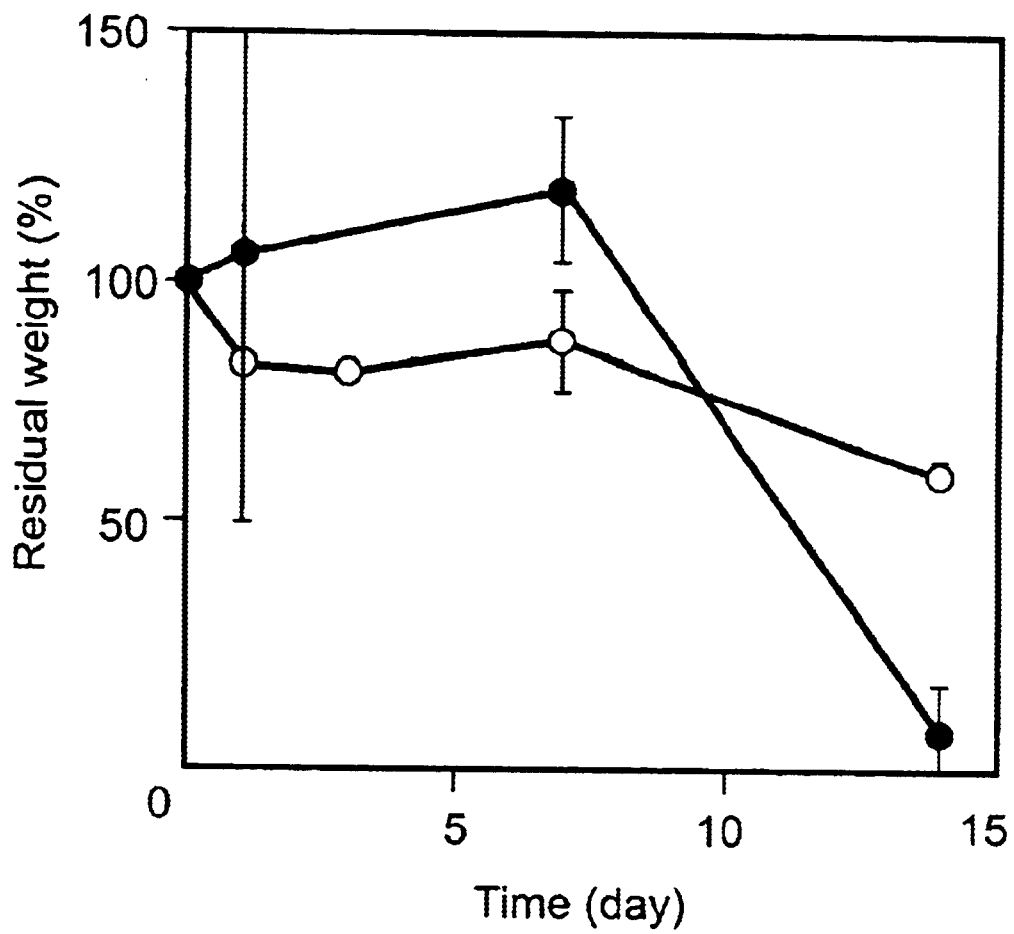
FIG. 7 shows time courses of residual amounts of crosslinked gelatin gel preparations (bFGF 100 µg) with different water contents, after mouse subcutaneous implantation.

The bFGF-containing crosslinked gelatin gel preparations of crosslinked gelatin gels having various water contents, prepared in Examples 5 and 6, were subcutaneously implanted in back portions of mice, to study an influence of the water content of the crosslinked gelatin gel on the in vivo vascularization activity of bFGF. FIGS. 5 and 6 show the results on the 7th day and 14 days after the preparations were implanted. As a control, separately, 100 μl of a phosphate buffer solution (pH 7.4) containing 100 μg of bFGF was subcutaneously administered. The dotted line in each Figure shows the hemoglobin amount of an untreated group. As shown in FIGS. 5 and 7, on the 7th day after the preparations were implanted, the gel having any water content showed a hemoglobin amount of a significantly high value as compared with the administration with a bFGF aqueous solution. Further, the hemoglobin amount was dependent upon the water content of the crosslinked gelatin gel, and the hemoglobin amount increased with a decrease in the water content. On the other hand, on the 14th day after the preparations were implanted, only the preparations of the crosslinked gelatin gel having a water content of less than 90% showed high hemoglobin amounts, while the preparations of the crosslinked gelatin gel having a water content higher than the above showed hemoglobin amounts which had decreased to the level of an untreated group. It is considered that when the water content is low, the decomposition of the crosslinked gelatin gel is slow and that on the 14th day, bFGF undergoes sustained release from the gel to exhibit its effect.

(Test Example 6)

The bFGF-containing crosslinked gelatin gel preparations of the crosslinked gelatin gels having water contents of 95.9 and 77.5%, obtained in Example 5, were studied for their degradation in mouse subcutaneous portion. FIG. 7 shows the results. The degradation was evaluated in the same manner as in Test Example 3. In both the gels having the above water contents, the decomposition proceeded with time. However, the degradation was dependent upon the water content, and the lower the water content is, the more difficult the decomposition is.

(Test Example 7)

Figure 8:
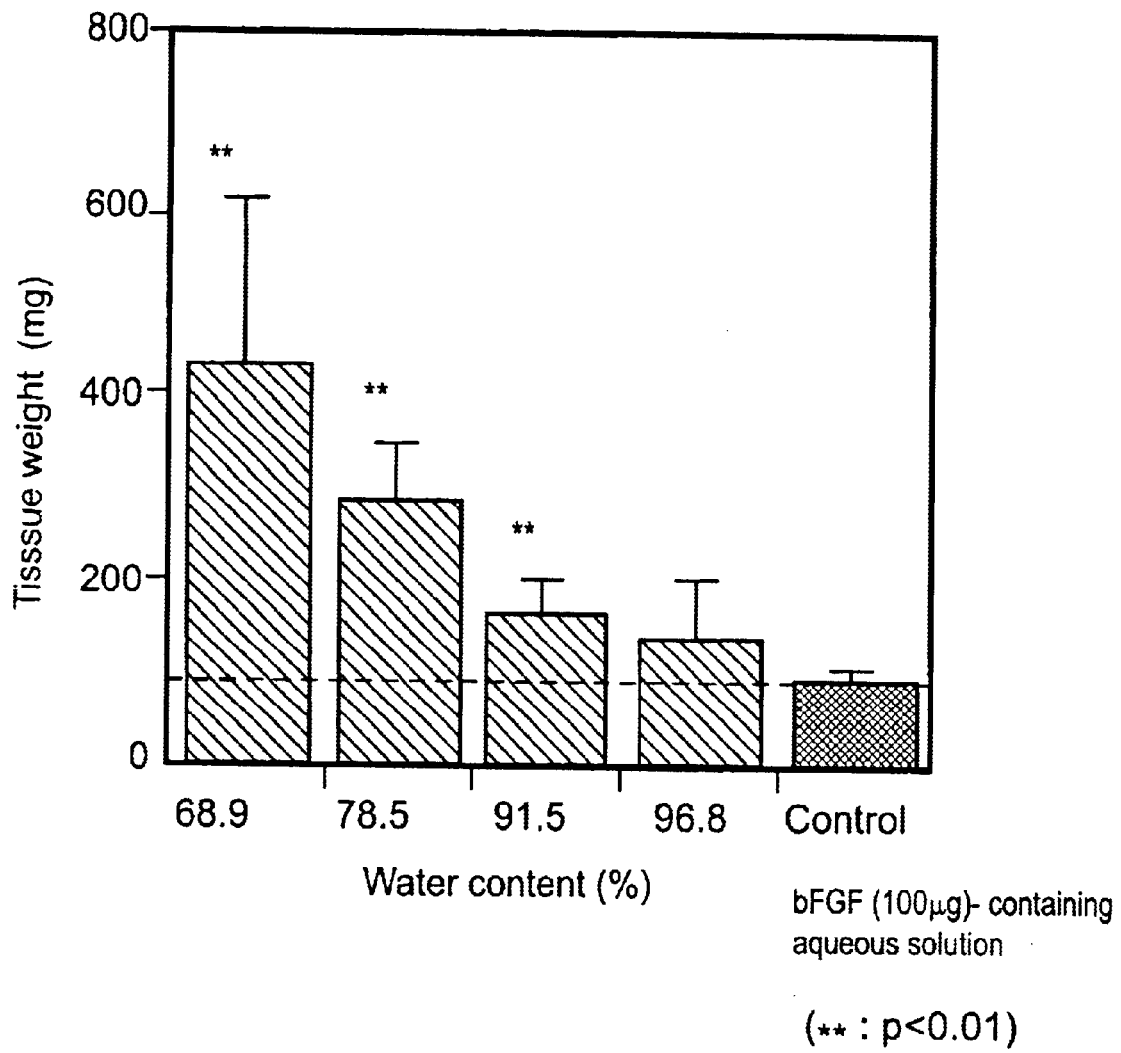
FIG. 8 shows a relationship between granulation tissue formation and the water content of a gel on the 7th day after the subcutaneous implantation of crosslinked gelatin gel preparations (bFGF 100 µg) in a mouse.

The bFGF-containing crosslinked gelatin gel preparations obtained in Examples 7 and 8 were implanted in the back portions of mice to study in influence of the water content of the crosslinked gelatin gel on the in vivo encapsulation activity of bFGF. The encapsulation activity of bFGF was studied as follows. Seven days after the preparations were implanted, tissues below the skin of the preparation-implanted site and on the nortal-muscular side were scraped off with a scalpel such that the scraped portion had a square form measuring 2 cm horizontally and vertically with the preparation-implanted site as a center. These tissues were measured for a weight in a wet state, to evaluate the encapsulation effect. FIG. 8 shows the results. The dotted line in FIG. 8 shows the level of an untreated group. As a result, it was found that the administration with bFGF contained in the crosslinked gelatin gel had an effect on the promotion of encapsulation of bFGF and that the portion around the preparation-implanted site was covered with an capsular layer. Further, the thickness of the capsular layer increased with a decrease in the water content of the crosslinked gelatin gel. In contrast, in the control group of mice which had been administered with 100 μg of bFGF in an aqueous solution state, no encapsulation was found around the administration site. As described above, it was been also found that when the activity of bFGF is evaluated in terms of encapsulation activity, the activity of bFGF can be enhanced by including the bFGF in the crosslinked gelatin gel to convert it to a sustained release one.

(Text Example 8)

The bFGF-containing crosslinked gelatin gel particle preparation obtained in Example 9 was subcutaneously administered to the back portions of mice by injection. One week after the administration, the skins of the mice were peeled off to observe the degree of vascularization in the particle preparation-administration site. As a result, it was found that since the portion around the particle preparation-administration site was red, the vascularization occurred. As described above, it is seen that the present invention produces the effect of the present invention regardless of the form of the crosslinked gelatin gel which is a carrier for containing bFGF, i.e., even if the crosslinked gelatin gel has a spherical or particulate form having an injectable size.

(Text Example 9)

The crosslinked gelatin gel particles (water content 87%) obtained in Example 13, in an amount of 3.7 mg, were impregnated with 100 μg of bFGF at 4° C. for a whole day and night, and then suspended in a saline solution, and the suspension was injected into rat ilium. After 2 weeks, the ilium were taken out and measured for a bone mineral content fluctuation. The term "bone mineral content" is an index for measuring the degree of an increase and a decrease of a bone, and specifically, it was measured with a bone-salt measuring apparatus (model DCS-600, supplied by Aloka Co. Ltd.). Further, a group of rats which were administered with an aqueous solution containing 100 µg of bFGF by injection was used as a control group, and similarly measured for a bone mineral content fluctuation. As a result, the group of rats which has been administered with the crosslinked gelatin gel particle preparation showed an increase in the bone mineral content by 15.7 mg, while the control group of rats which had been administered with a bFGF-containing aqueous solution showed an increase by 7.1 mg. As compared with the control group, the group of rats which has been administered with the bFGF-containing crosslinked gelatin gel particles of the present invention showed a remarkable increase in the bone mineral content, and as compared with the aqueous solution preparation, the sustained release preparation formed of the crosslinked gelatin gel showed significant ossification activity.

(Test Example 10)

Leg portions of rats were cut open to expose bones, and the fibula were cut apart with bone scissors. The bFGF-containing crosslinked gelatin gel preparation obtained in Example 16 was implanted in the cut-apart portions, and the portions were sutured. After 3 weeks, the cut fibula of the rats were studied for increases in the bone mineral content and bone density. As a control, an aqueous solution containing bFGF in the same amount as that of the above preparation was administered to rats. Table 2 shows the results.

TABLE 2

| bFGF dosage (µg/preparation | Bone mineral content (mg) | |
|---|---|---|
| or aqueous solution) | Crosslinked gelatin gel preparation | Aqueous solution |
| 0 | 9.5 ± 1.7 | 9.4 ± 1.7 |
| 2 | 14.4 ± 2.1 | 11.3 ± 3.2 |
| 10 | 17.6 ± 3.2 | 12.0 ± 3.1 |

The results in the above Table 2 show that the bFGF crosslinked gelatin gel preparation of the present invention promoted a high increase in the bone mineral content as compared with the group of rats which had been administered with the bFGF aqueous solution. These data has shown that the crosslinked gelatin gel preparation of the present invention is useful for the therapy of fracture and osteoanagenesis since it undergoes sustained release from the gel to promote an increase in the bone mineral content.

EFFECT OF THE INVENTION

According to the present invention, bFGF-containing crosslinked gelatin gel preparations having different water contents, i.e., having different in vivo decomposition and absorption properties, can be prepared by changing the preparation conditions of the crosslinked gelatin gel which is a sustained release carrier. bFGF which undergoes sustained release from the crosslinked gelatin gel preparations of the present invention has physiological activities. Further, the decomposition rate of the crosslinked gelatin gel is changed by changing the water content of the crosslinked gelatin gel which is a sustained release carrier, and the sustained release time of bFGF can be changed. As a result, the persistency of in vivo activity expression of bFGF can be controlled. Further, the above effects of the present invention are exhibited regardless of the kind of gelatins and the form of the preparations.

What is claimed is:

1. A method of treating a fracture comprising administering to an animal in need of same a therapeutically effective, fracture treating amount of basic fibroblast growth factor impregnated in a water insoluble, in vivo degradable cross-linked gelatin gel for sustained release of the basic fibroblast growth factor, the cross-linked gelatin gel having a water content of 63.1 to 99% w/w and produced by process comprising the steps of:

(a) cross-linking an alkali-treated gelatin having an isoelectric point of 4.9 to provide a cross-linked, water-insoluble gelatin gel;

(b) lyophilizing or drying the cross-linked, water-insoluble gelatin gel of step (a); and (c) incorporating basic fibroblast growth factor into the cross-linked, water-insoluble gelatin gel of step (b).

2. A method of treating osteoporosis comprising administering to an animal in need of same a therapeutically effective, osteoporosis treating amount of basic fibroblast growth factor impregnated in a water insoluble, in vivo degradable cross-linked gelatin gel for sustained release of the basic fibroblast growth factor, the cross-linked gelatin gel having a water content of 63.1 to 99% w/w and produced by a process comprising the steps of:

(a) cross-linking an alkali-treated gelatin having an isoelectric point of 4.9 to provide a cross-linked, water-insoluble gelatin;

(b) lyophilizing or drying the cross-linked, water-insoluble gelatin gel of step (a); and (c) incorporating basic fibroblast growth factor into the cross-linked, water-insoluble gelatin gel of step (b).

3. A method of promoting vascularization comprising administering to an animal in need of same a therapeutically effective, vascularization promoting amount of basic fibroblast growth factor impregnated in a water insoluble, in vivo degradable cross-linked gelatin gel for sustained release of the basic fibroblast growth factor, the cross-linked gelatin gel having a water content of 63.1 to 99% w/w and produced by a process comprising the steps of:

(a) cross-linking an alkali-treated gelatin having an isoelectric point of 4.9 to provide a cross-linked, water-insoluble gelatin gel;

(b) lyophilizing or drying the cross-linked, water-insoluble gelatin gel of step (a); and (c) incorporating basic fibroblast growth factor into the cross-linked, water-insoluble gelatin gel of step (b).

4. The method of claim 1, 2 or 3 wherein the basic fibroblast growth factor in water insoluble cross-linked gelatin gel is administered topically.

5. The method of claim 1, 2 or 3 wherein the basic fibroblast growth factor in water insoluble cross-linked gelatin gel is implanted within the animal's body.

6. The method of claim 5 wherein the basic fibroblast growth factor impregnated water insoluble cross-linked gelatin gel is in the form of a cylinder, prism, sheet, disc, sphere or fine particles.

7. The method of claim 1, 2 or 3 wherein the basic fibroblast growth factor in water insoluble cross-linked gelatin gel is injected into bone.

8. The method of claim 1, 2 or 3 wherein the basic fibroblast growth factor in water insoluble cross-linked gelatin gel is implanted into bone.

9. The method of claim 1, 2 or 3 wherein the gel is cross-linked with glutaraldehyde or a water-soluble carbodiimide.

10. The method of claim 1, 2 or 3 wherein the basic fibroblast growth factor has the amino acid sequence of SEQ ID NO:1 or SEQ ID NO:2.

11. A method of delivering and releasing basic fibroblast growth factor to an animal requiring same comprising administering to the desired site an effective amount of basic fibroblast growth factor impregnated in a water-insoluble, in-vivo degradable cross-linked gelatin gel obtained by reacting alkali-treated gelatin with a cross-linker for sustained release of the basic fibroblast growth factor, the cross-linked gelatin gel having a water content of 63.1 to 99% w/w and produced by a process comprising the steps of:

(a) cross-linking an alkali treated gelatin having an isoelectric point of 4.9 to provide a cross-linked, water-insoluble gelatin gel;

(b) lyophilizing or drying the cross-linked, water-insoluble gelatin gel of step (a); and (c) incorporating basic fibroblast growth factor into the cross-linked, water-insoluble gelatin gel of step (b).

12. A process of preparing an in vivo degradable, water-insoluble cross-linked gelatin gel impregnated with basic fibroblast growth factor for sustained release of the basic fibroblast growth factor, comprising the steps of:

(a) cross-linking an alkali-treated gelatin having an isoelectric point of 4.9 to provide a cross-linked, a water-insoluble gelatin gel having a water content of 63.1 to 99% w/w;

(b) lyophilizing and drying the cross-linked, water-insoluble gelatin gel of step (a); and (c) incorporating basic fibroblast growth factor into the cross-linked, water-insoluble gelatin gel of step (b);

thereby providing a basic fibroblast growth factor-impregnated in vivo degradable, water-insoluble cross-linked gelatin gel to deliver basic fibroblast growth factor to a desired site to release and delivery same.

* * * * *

UNITED STATES PATENT AND TRADEMARK OFFICE
CERTIFICATE OF CORRECTION

PATENT NO. : 6,831,058 B1
DATED : December 14, 2004
INVENTOR(S) : Ikada et al.

It is certified that error appears in the above-identified patent and that said Letters Patent is hereby corrected as shown below:

<u>Title page,</u>
Item [75], Inventors, should read -- Yoshito Ikada, Kyoto (JP); Yasuhiko Tabata, Kyoto (JP); Shigeki Hijikata, Shizuoka (JP); Makoto Tamura, Shiga (JP) --.

Signed and Sealed this

Thirtieth Day of May, 2006

JON W. DUDAS
*Director of the United States Patent and Trademark Office*

SEQUENCE LISTING (1) GENERAL INFORMATION:

(iii) NUMBER OF SEQUENCES:    2

(2) INFORMATION FOR SEQ ID NO:1:

(i) SEQUENCE CHARACTERISTICS:
        (A) LENGTH:              154 AMINO ACIDS
        (B) TYPE:                AMINO ACID
        (D) TOPOLOGY: Not Relevant (ii) MOLECULE TYPE:       POLYPEPTIDE (vi) ORIGINAL SOURCE:
        (A) ORGANISM:            HOMO SAPIEN (ix) FEATURE:
        (A) NAME/KEY:            MODIFIED bFGF -continued

```
(x) PUBLICATION INFORMATION:
    (H) DOCUMENT NUMBER: PCT PUBLICATION WO 87/01728
    (J) FILING DATE: 1987
```

(xi) SEQUENCE DESCRIPTION: SEQ ID NO: 1:

```
Ala Ala Gly Ser Ile Thr Thr Leu Pro Ala Leu Pro Glu Asp Gly
 1               5                  10                  15

Gly Ser Gly Ala Phe Pro Pro Gly His Phe Lys Asp Pro Lys Arg
                20                  25                  30

Leu Tyr Cys Lys Asn Gly Gly Phe Phe Leu Arg Ile His Pro Asp
                35                  40                  45

Gly Arg Val Asp Gly Val Arg Glu Lys Ser Asp Pro His Ile Lys
                50                  55                  60

Leu Gln Leu Gln Ala Glu Glu Arg Gly Val Val Ser Ile Lys Gly
                65                  70                  75

Val Cys Ala Asn Arg Tyr Leu Ala Met Lys Glu Asp Gly Arg Leu
                80                  85                  90

Leu Ala Ser Lys Cys Val Thr Asp Glu Cys Phe Phe Phe Glu Arg
                95                 100                 105

Leu Glu Ser Asn Asn Tyr Asn Thr Tyr Arg Ser Arg Lys Tyr Thr
               110                 115                 120

Ser Trp Tyr Val Ala Leu Lys Arg Thr Gly Gln Tyr Lys Leu Gly
               125                 130                 135

Ser Lys Thr Gly Pro Gly Gln Lys Ala Ile Leu Phe Leu Pro Met
               140                 145                 150

Ser Ala Lys Ser
```

(2) INFORMATION FOR SEQ ID NO:2:

(i) SEQUENCE CHARACTERISTICS:
        (A) LENGTH:                   153 AMINO ACIDS
        (B) TYPE:                     AMINO ACID
        (D) TOPOLOGY: Not Relevant (ii) MOLECULE TYPE:         POLYPEPTIDE (vi) ORIGINAL SOURCE:
        (A) ORGANISM:              HOMO SAPIEN (ix) FEATURE:
        (A) NAME/KEY:              MODIFIED bFGF (x) PUBLICATION INFORMATION:
        (H) DOCUMENT NUMBER: PCT PUBLICATION WO 87/01728
        (J) FILING DATE: 1987

(xi) SEQUENCE DESCRIPTION: SEQ ID NO: 2:

```
Ala Gly Ser Ile Thr Thr Leu Pro Ala Leu Pro Glu Asp Gly Gly
             5                  10                  15

Ser Gly Ala Phe Pro Pro Gly His Phe Lys Asp Pro Lys Arg Leu
            20                  25                  30

Tyr Cys Lys Asn Gly Gly Phe Phe Leu Arg Ile His Pro Asp Gly
            35                  40                  45

Arg Val Asp Gly Val Arg Glu Lys Ser Asp Pro His Ile Lys Leu
            50                  55                  60

Gln Leu Gln Ala Glu Glu Arg Gly Val Val Ser Ile Lys Gly Val
            65                  70                  75

Cys Ala Asn Arg Tyr Leu Ala Met Lys Glu Asp Gly Arg Leu Leu
            80                  85                  90

Ala Ser Lys Cys Val Thr Asp Glu Cys Phe Phe Phe Glu Arg Leu
            95                 100                 105

Glu Ser Asn Asn Tyr Asn Thr Tyr Arg Ser Arg Lys Tyr Thr Ser
```

```
                        110                 115                 120
Trp Tyr Val Ala Leu Lys Arg Thr Gly Gln Tyr Lys Leu Gly Ser
                125                 130                 135
Lys Thr Gly Pro Gly Gln Lys Ala Ile Leu Phe Leu Pro Met Ser
                140                 145                 150
Ala Lys Ser
```